(12) United States Patent
Satake

(10) Patent No.: US 8,733,932 B2
(45) Date of Patent: May 27, 2014

(54) OPHTHALMIC ULTRASONIC DIAGNOSING APPARATUS

(75) Inventor: Miyuki Satake, Aichi-ken (JP)

(73) Assignee: Nidek Co., Ltd., Gamagori-Shi, Aichi-Ken (JP)

( * ) Notice: Subject to any disclaimer, the term of this patent is extended or adjusted under 35 U.S.C. 154(b) by 817 days.

(21) Appl. No.: 12/696,437

(22) Filed: Jan. 29, 2010

(65) Prior Publication Data

US 2010/0198074 A1 Aug. 5, 2010

(30) Foreign Application Priority Data

Jan. 30, 2009 (JP) .................................. 2009-19571

(51) Int. Cl.
*A61B 3/10* (2006.01)
*A61B 5/05* (2006.01)

(52) U.S. Cl.
USPC ......................................... 351/205; 600/407

(58) Field of Classification Search
USPC .......... 351/205, 206, 210, 221, 246; 600/407; 601/2
See application file for complete search history.

(56) References Cited

U.S. PATENT DOCUMENTS

| 7,455,406 B2 | 11/2008 | Miwa et al. |
| 2008/0079898 A1* | 4/2008 | Miwa et al. .................... 351/205 |
| 2009/0164007 A1* | 6/2009 | Van Heugten ............... 623/6.11 |

FOREIGN PATENT DOCUMENTS

| JP | 2001-187022 | 7/2001 |
| JP | 2008-029468 | 2/2008 |
| JP | 2008-086527 | 4/2008 |

\* cited by examiner

*Primary Examiner* — Elmer Chao
(74) *Attorney, Agent, or Firm* — Muncy, Geissler, Olds & Lowe, P.C.

(57) ABSTRACT

An ophthalmic ultrasonic diagnosing apparatus for measuring an ocular axial length of an examinee's eye includes an ultrasonic probe for A-mode measurement including a transducer arranged to emit an ultrasonic wave toward the inside of the eye, and receive return echoes from eye constituent parts, and an analysis unit for identifying, by analyzing signals of the received echoes, the respective signals as a return echo signal from a cornea of the eye, a return echo signal from an intraocular lens implanted in the eye, multiple return echo signals produced from the signals repeatedly returning between the intraocular lens and the transducer, and a return echo signal from a retina of the eye, while distinguishing the retinal signal from the multiple signals based on a property shown by the multiple signals and/or a property shown by the retinal signal, and calculate the axial length based on the corneal and retinal signals.

5 Claims, 4 Drawing Sheets

OPHTHALMIC ULTRASONIC DIAGNOSING APPARATUS

BACKGROUND OF THE INVENTION

1. Field of the Invention

The present invention relates to an ophthalmic ultrasonic diagnosing apparatus for measuring an ocular axial length of an examinee's eye or the sizes of constituent parts of the eye.

2. Description of Related Art

Conventionally, there is known an ophthalmic ultrasonic diagnosing apparatus for measuring an ocular axial length that is arranged to obtain the positions of constituent parts of an eyeball by transmitting an ultrasonic wave from a transducer included in an ultrasonic probe to the constituent parts, and receiving to process return echoes therefrom, and measure the ocular axial length (see Japanese Patent Publication Laid-Open No 2001-187022). It is to be noted that the ocular axial length is basic data to be used for prescribing an intraocular lens (hereinafter, referred to as an IOL), which is to be implanted in an eye after an opaque crystalline lens of a cataract is removed therefrom.

Specifically, in the measurement of the ocular axial length of a phakic eye, the apparatus identifies a return echo 102 that exceeds a detection level 106a first from the anterior-segment side of the eye as the return echo from the cornea, a return echo 103a that exceeds the detection level 106a second as the return echo from the front surface of the crystalline lens, and a return echo 103b that exceeds the detection level 106a third as the return echo from the rear surface of the crystalline lens, as shown in FIG. 4. Then, the apparatus identifies a return echo 104 that exceeds a detection level 106b first behind a position P1 located a predetermined distance W apart from the position of the cornea (the predetermined distance W is 12 mm, for example, which is established such that the return echoes within the predetermined distance W are distinguished from a return echo from the retina) as the return echo from the retina. Based on a distance between a rising position 107 of the corneal return echo 102 and a rising position 109 of the retinal return echo 104, the apparatus automatically obtains the ocular axial length.

If the return echoes from the constituent parts of the anterior segment and the retina are difficult to be identified automatically, manual measurement may be carried out such that an examiner observes waveforms of the return echoes (A-mode waveforms) displayed on a display and manually establishes gates to identify the positions of the constituent parts based on the examiner's experience (see Japanese Patent Publication Laid-Open No. 2008-29468).

In the measurement of the ocular axial length of an eye with previously implanted IOL (hereinafter, referred to as an IOL implanted eye), which is a case where a new IOL is prescribed to an examinee having an IOL implanted eye, the return echo 103b from the rear surface of the crystalline lens as shown in FIG. 4 does not appear but instead multiple return echoes could remarkably appear subsequent to a return echo from the IOL because an ultrasonic signal repeatedly returns between the IOL and the tip (the transducer) of the ultrasonic probe (or the cornea). The appearance of the multiple return echoes result from a great difference between physical properties of the eye constituent parts and the IOL.

However, the use of the above-described criteria of the identification of the retinal position for the IOL implanted eye leads to false detection of the multiple return echoes as the retinal return echo, and a wrong measurement result is output. If the examiner is not capable of recognizing occurrence of the multiple return echoes, the examiner cannot notice the fact that the ocular axial length is wrongly measured, and accordingly cannot prescribe an IOL with correct power. The function of the manual measurement such that the examiner manually establishes the gates is sometimes used according to the circumstances; however, it remains difficult to distinguish the multiple return echoes from the retinal return echo.

SUMMARY OF THE INVENTION

An object of the invention is to overcome the problems described above and to provide an ophthalmic ultrasonic diagnosing apparatus that is capable of decreasing the possibility of false detection of a multiple return echo as a retinal return echo in an IOL implanted eye, and performing more accurate measurement of an ocular axial length.

To achieve the objects and in accordance with the purpose of the present invention, an ophthalmic ultrasonic diagnosing apparatus for measuring an ocular axial length of an examinee's eye includes an ultrasonic probe for A-mode measurement including a transducer that is arranged to emit an ultrasonic wave toward the inside of the eye, and receive return echoes from constituent parts inside the eye, and an analysis unit that is arranged to identify, by analyzing signals of the received return echoes, the respective return echo signals as a return echo signal from a cornea of the eye, a return echo signal from an intraocular lens that is implanted in the eye, multiple return echo signals that are produced from the return echo signals that repeatedly return between the intraocular lens and the transducer, and a return echo signal from a retina of the eye, while distinguishing the retinal return echo signal from the multiple return echo signals based on at least one of a property shown by the multiple return echo signals and a property shown by the retinal return echo signal, and calculate the ocular axial length based on the corneal return echo signal and the retinal return echo signal.

Additional objects and advantages of the invention are set forth in the description which follows, are obvious from the description, or may be learned by practicing the invention. The objects and advantages of the invention may be realized and attained by the ophthalmic ultrasonic diagnosing apparatus in the claims.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

DETAILED DESCRIPTION OF THE PREFERRED EMBODIMENTS

Figure 1:
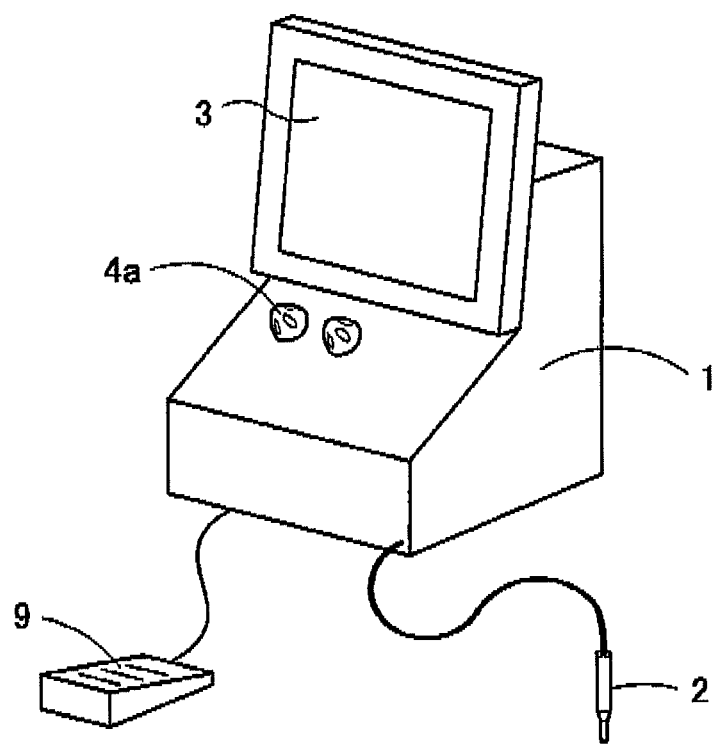
FIG. 1 is an external schematic view showing an ophthalmic ultrasonic diagnosing apparatus according to a preferred embodiment of the present invention.

An ophthalmic ultrasonic diagnosing apparatus according to a preferred embodiment of the present invention is described below with reference to the accompanying drawings. FIG. 1 is an external schematic view showing an ophthalmic ultrasonic diagnosing apparatus according to the preferred embodiment of the present invention. In FIG. 1, a main body 1 of the apparatus is connected with an ultrasonic probe 2 for A-mode, and a large liquid crystal display panel 3 capable of displaying in color is provided on a front surface of the main body 1. The display panel 3 has a touch panel function, and is arranged such that an examiner can establish various conditions by performing selecting operation of settings displayed on the display panel 3. The main body 1 is connected with a foot switch 9 that is arranged to send a measurement starting signal. In addition, the main body 1 is provided with a gain adjustment switch 4a.

Figure 2:
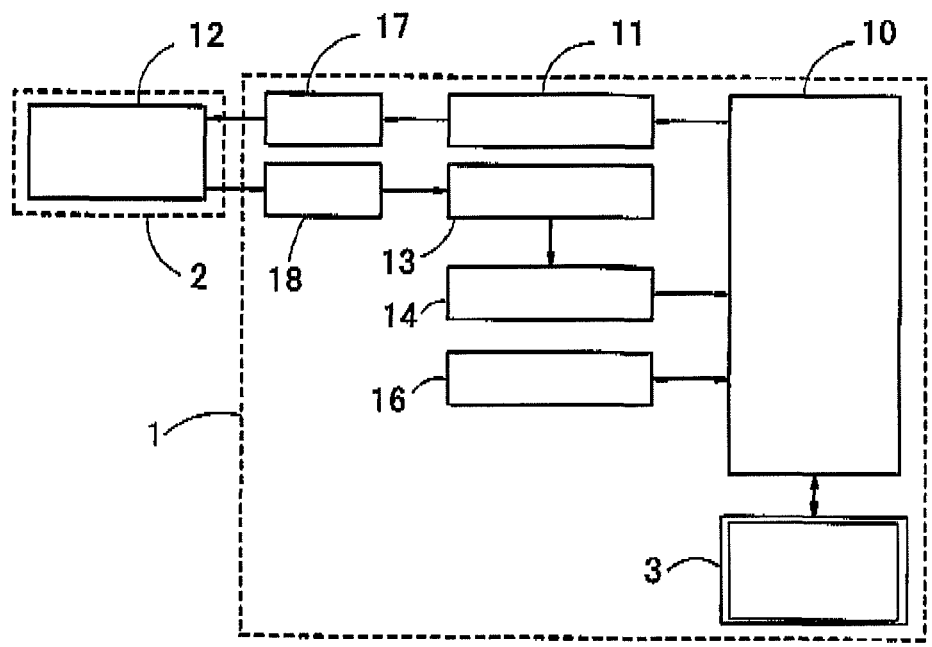
FIG. 2 is a schematic control block diagram of the apparatus.

FIG. 2 is a schematic control block diagram of the ophthalmic ultrasonic diagnosing apparatus. A control unit 10 is incorporated in the main body 1, and is arranged to control various circuits and constituent elements. The control unit 10 is arranged to drive and control a clock generation circuit 11 to emit an ultrasonic wave from a transducer 12 via a transmitter 17, the transducer 12 being provided in the probe 2. An A/D converter 13 is arranged to convert return echoes from constituent parts of an examinee's eye that are received by the transducer 12 into digital signals via an amplifier 18. A sampling memory 14 is arranged to store the digital signals of the return echoes. The control unit 10 functions also as an analysis unit that is arranged to analyze the return echo signals stored in the sampling memory 14 to identify the positions of the constituent parts, and measure, by calculating the length from the position of the cornea to the position of the retina, an ocular axial length of the eye. The measurement result is displayed on the display panel 3. A reference value to be used when gain adjustment is automatically made is prestored in a memory 16.

Figure 3:
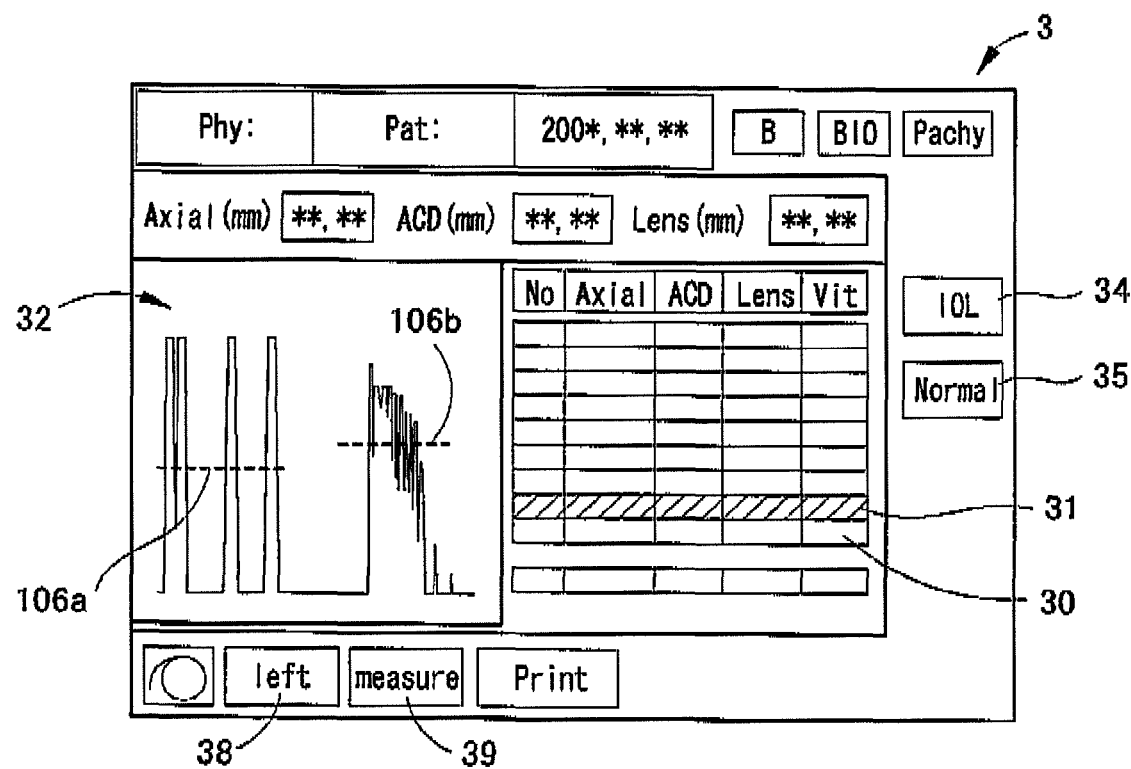
FIG. 3 is a view showing an example of a measurement screen displayed on a screen of a display panel of the apparatus.

FIG. 3 is a view showing an example of a measurement screen displayed on a screen of the display panel 3. An examinee's eye switch 34 for switching the types of the examinee's eye is provided in the right-hand part of the measurement screen. With the use of the switch 34, switching is performed between a measurement mode of measuring the ocular axial length of a phakic eye and a measurement mode of measuring the ocular axial length of an IOL implanted eye. A right/left eye switch 38 for switching display of the examinee's eyes between the right eye and left eye, and a measurement switch 39 for starting and stopping the ocular axial length measurement are provided in the bottom left-hand part of the measurement screen.

In addition, a list 30 of results of measurement in A-mode that is performed more than one time (e.g., 10 times) with respect to examinees' eyes is displayed on the screen (the list 30 indicates, from the left, ID numbers, ocular axial lengths, depths of anterior chambers, thicknesses of crystalline lenses, and lengths of vitreous bodies). A-mode waveforms 32 that correspond to the measurement results selected by a cursor 31 are displayed at the left of the list 30. A detection level 106a that is used for detecting the positions of the constituent parts of the anterior-segment side of the eye, and a detection level 106b that is used for detecting the retinal position of the eye are displayed on the A-mode waveforms 32. Based on the positions at which the return echoes exceed the detection level 106a or 106b, the return echoes are identified as the respective return echoes from the constituent parts. It is to be noted that the levels of the detection levels 106a and 106b can be changed with the use of a detection level-changing switch 35 provided in the right-hand part of the measurement screen.

Figure 4:
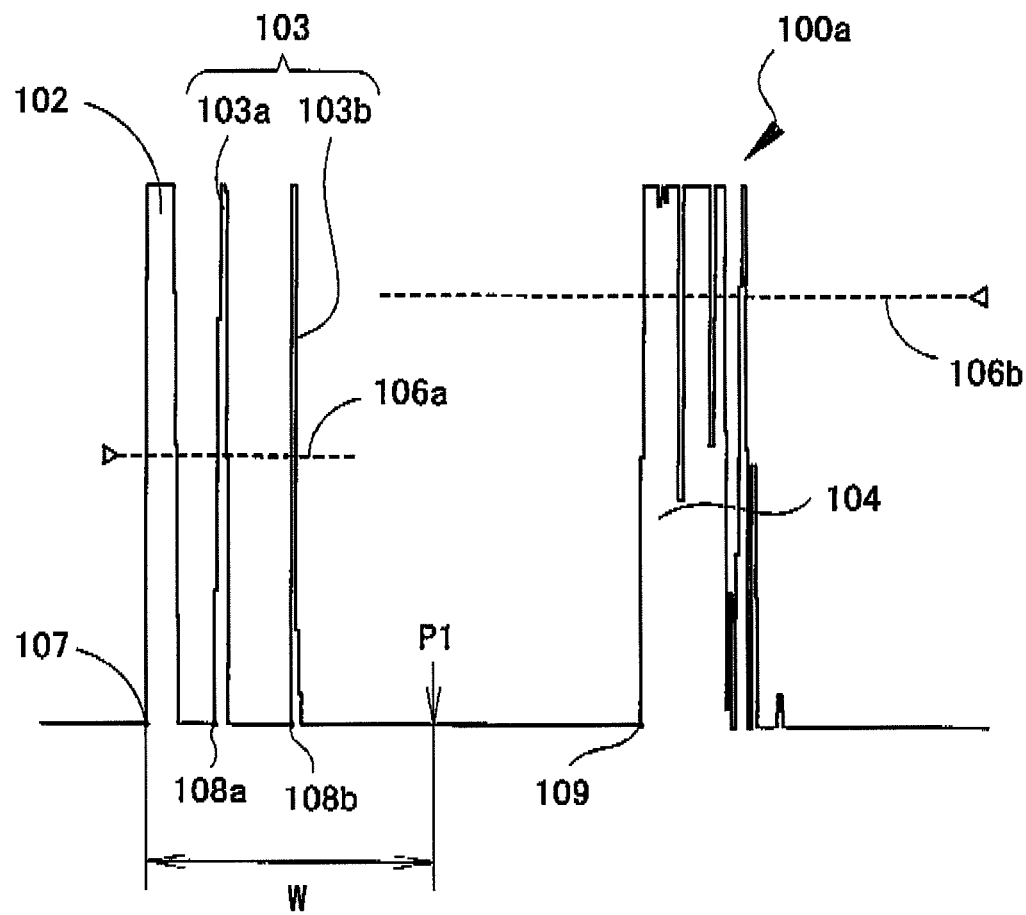
FIG. 4 is a view showing an example of A-mode waveforms of a phakic eye.

FIG. 4 is a view showing an example of A-mode waveforms 100a of a phakic eye. A return echo 102 from the cornea of the eye, a return echo 103 from the crystalline lens of the eye (a return echo 103a from the front surface of the crystalline lens and a return echo 103b from the rear surface of the crystalline lens), and a return echo 104 from the retina of the eye are found on the A-mode waveforms 100a.

A brief description of measurement in the phakic eye measurement mode will be provided. When the phakic eye measurement mode is set with the use of the switch 34, the control unit 10 makes a search of the sampling data stored in the sampling memory 14 from the corneal side, identifies a return echo 102 that exceeds the detection level 106a first as the return echo from the cornea, and identifies a rising position 107 of the return echo 102 as the position of the cornea. Similarly, the control unit 10 identifies a return echo 103a that exceeds the detection level 106a second as the return echo from the front surface of the crystalline lens, and identifies a rising position 108a of the return echo 103a as the position of the front surface of the crystalline lens. Similarly, the control unit 10 identifies a return echo 103b that exceeds the detection level 106a third as the return echo from the rear surface of the crystalline lens, and identifies a rising position 108b of the return echo 103b as the position of the rear surface of the crystalline lens. In addition, concerning the retinal return echo 104, the control unit 10 starts a search from a position P1 located a predetermined distance W (e.g., 12 mm) apart from the corneal position 107, identifies the return echo 104 that exceeds the detection level 106b first as the return echo from the retina, and identifies a rising position 109 of the return echo 104 as the position of the retina.

Figure 5:
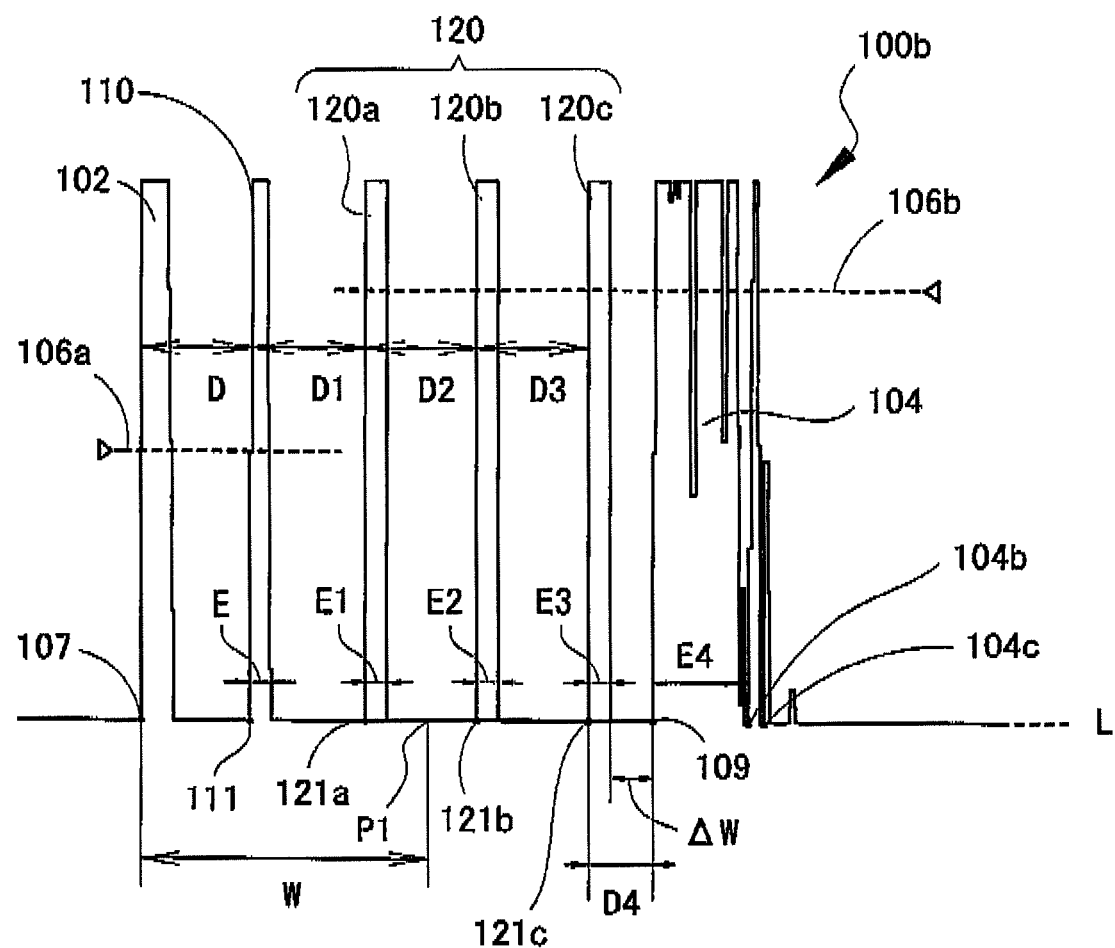
FIG. 5 is a view showing an example of A-mode waveforms of an IOL implanted eye.

Next, a description of a case where the IOL implanted eye measurement mode is set with the use of the switch 34 will be provided. FIG. 5 is a view showing an example of A-mode waveforms 100b of an IOL implanted eye. On the A-mode waveforms 100b, a return echo 110 from the IOL appears subsequent to the corneal return echo 102, three return echoes 120a, 120b and 120c that are multiple return echoes 120 further appear, and the return echo 104 appears subsequent to the return echo 120c, the return echo 104 being the retinal return echo. This is because, compared with a crystalline lens (having a thickness of about 4 mm), the IOL is about 0.8 mm in thickness, a return echo from the front surface of the IOL and a return echo from the rear surface of the IOL are not separate, which is different from the case of the phakic eye, and the return echoes appear as one group of return echoes.

A description of a first identification method for identifying the return echo 104 as the retinal return echo as distinguished from the multiple return echoes 120 will be provided referring to the waveforms shown in FIG. 5. The first identification method uses the periodicity of the return echoes, considering a property shown uniquely by the signals of the multiple return echoes 120. The multiple return echoes 120 appear at almost regular intervals because an ultrasonic signal repeatedly returns between the IOL and the tip (transducer) of the ultrasonic probe 2 (or the cornea) to produce the multiple return echoes 120. Being returns from the front surface and the rear surface inside the IOL, the waveforms of the return echoes 120a, 120b and 120c tend to appear, each having a width (a distance, a time) same as the waveform of the IOL return echo 110.

The control unit 10 starts a search of the sampling data of the return echo signals that is stored in the sampling memory 14 from the anterior-segment side, and detects rising positions of the return echoes that exceed the detection level 106a. The rising position 107 of the return echo 102 that exceeds the detection level 106a first is identified as the corneal position, and a rising position 111 of the return echo 110 that exceeds the detection level 106a second is identified as the position of the IOL.

Upon identification of the IOL position 111, a search is made to know whether multiple return echoes are produced closer to the retinal side than the IOL position 111. The control unit 10 calculates a distance D that is a difference between the corneal position 107 (the corneal front-surface position) and the IOL position 111 (the IOL front-surface position). Then, the control unit 10 calculates a distance D1 between the IOL position 111 and a rising position 121a of the return echo 120a that is subsequently detected, and in a similar manner calculates a distance D2 between the adjacent return echo 120a and return echo 120b, a distance D3 between the adjacent return echo 120b and return echo 120c, and a distance D4 between the adjacent return echo 120c and return echo 104, successively.

The control unit 10 establishes a permissible distance D0 that is obtained by adding a tolerate margin of error (e.g., ±10% of the distance D) to the distance D, and judges whether the distance D1, D2, D3 or D4 falls within the permissible distance D0. When the distance D1 falls within the distance D0 and the distance D2 also falls within the distance D0 as shown in FIG. 5, the return echo 120a is identified as one of the multiple return echoes 120. When the subsequent distance D3 also falls within the distance D0, the return echo 120b is identified as one of the multiple return echoes 120. Then, when the subsequent distance D4 does not fall within the distance D0, the return, echoes 120a to 120c are identified as the multiple return echoes 120, and the return echo 104 that appears subsequently is identified as the retinal return echo. Thus, distinguishing the retinal return echo 104 from the multiple return echoes 120 appearing previous to the retinal return echo 104, the control unit 10 calculates an ocular axial length of the eye based on a rising position 109 of the retinal return echo 104 and the corneal position 107.

In addition to the above-described identification condition of the periodicity of the distances of the adjacent return echoes, establishment of another identification condition whether the widths of the waveforms of the return echoes are almost equal to each other improves accuracy in distinguishing the multiple return echoes from the retinal return echo. The control unit 10 successively obtains a width E of the waveform of the IOL return echo 110, widths E1, E2, E3 and E4 of the respective waveforms of the return echoes 120a, 120b, 120c and 104. Besides, the level at which the width E is obtained is preestablished between the zero level and the detection level 106a of which gains are adjusted.

The control unit 10 establishes a permissible width E0 that is obtained by adding a tolerate margin of error (the tolerate margin of error is established in a similar manner to the case of the distance D) to the width E. Identification in a case where the widths of the waveforms are added to the identification condition can be used as follows. There is a case where it is unclear whether or not the return echo 120c is a part of the retinal return echo 104 because the return echo 120c is close to the retinal return echo 104 and the distance D4 is accordingly very small; however, even in such a case, the width E4 of the retinal return echo 104 appears larger than the width E of the IOL return echo 110, so that if the width E3 of the return echo 120c is equal to the width E0 (the width E0 is almost equal to each width of the other multiple return echoes), the return echo 120c is identified as one of the multiple return echoes 120 with accuracy.

A description of a second identification method for identifying the return echo 104 as the retinal return echo as distinguished from the multiple return echoes 120 will be provided.

In the second identification method, a search of the return echoes is made from the retinal side in addition to the search of the return echoes from the anterior-segment side, and the retinal return echo 104 is distinguished from the multiple return echoes 120 by using a property shown uniquely by the signal of the retinal return echo 104. Through the search from the anterior-segment side (corneal side), the return echo 102 that exceeds the detection level 106a first is identified as the corneal return echo, and the return echo 110 that exceeds the detection level 106a second is identified as the IOL return echo in a similar manner as described above. The rising position 107 of the return echo 102 that exceeds the detection level 106a first is identified as the corneal position, and the rising position 111 of the return echo 110 that exceeds the detection level 106a second is identified as the IOL position.

Upon termination of the identification up to the IOL position, the control unit 10 makes the search from the retinal side. The search from the retinal side detects the retinal return echo 104 first at the detection level 106b. The retinal return echo has a property that its high-intensity signals (waveforms) have intricately-mixed risings and fallings. While the high-intensity signals inside the retina get more attenuated toward the rear as in ordinary cases, the high-intensity signals in the vicinity of the retinal front surface have a property of appearing as a high-intensity waveform having a width larger than the IOL return echo 110 in a state where gains of the high-intensity signals inside the retina are increased so as to exceed the detection level 106b. In addition, the high-intensity signals inside the retina have a property that the spacings among the waveforms of the retinal return echo at the zero-intensity level appear much narrower than the spacings among the waveforms of the multiple return echoes.

Hence, in order to distinguish the multiple return echoes from the retinal return echo, a predetermined distance Δd that is a criterion for determining the extent of the retinal return echo when the return echoes cross a zero line L is prestored in the memory 16. The distance Δd is a value that is preestablished based on an experiment or experience, and is 0.1 mm, for example.

Upon termination of the detection of the return echo 104 at the detection level 106b, the control unit 10 obtains positions where the waveform signals cross the zero line L (zero cross) (e.g., positions 104b, 104c, 109) successively from the retinal side in order to obtain the extent of the retinal return echo. Then, the control unit 10 makes a comparison of each distance ΔW among the signals at the zero crossing with the distance Δd successively from the retinal side, and determines, if the distance ΔW at the zero crossing is smaller than the distance Δd, a component of the waveform that includes the subsequent rising (i.e., a component of the waveform at the cornea side) as a part of the retinal return echo, while determines, if the distance ΔW at the zero crossing is larger than the distance Δd, a component of the waveform that includes the subsequent rising as not the retinal return echo. In the example shown in FIG. 5, since the distance ΔW between the return echo 104 and the return echo 120c is larger than the distance Δd, the control unit determines the return echo 120c as one of the multiple return echoes, and the subsequent return echo 104 as the retinal return echo. Alternatively, the widths of the high-intensity signals (waveforms) of the return echoes can be used as an identification condition of the retinal return echo. The control unit 10 makes a comparison of the width E of the waveform of the IOL return echo 110 with the width E4 of the waveforms of the return echo 104 that are regarded as successive components, and determines, if the width E4 is larger than the width E (it is also preferable that the width E4 is larger than a value that is obtained by adding a fixed value to the width E), the return echo 104 as the retinal return echo. Then, the control unit 10 identifies the rising position 109 of the return echo 104 as the retinal position.

The above-described identification of the corneal position 107 obtained through the search of the return echoes from the anterior-segment side, and identification of the retinal position 109 obtained through the search of the return echoes from the retinal side allow the ocular axial length to be calculated.

A description of a third identification method for identifying the return echo 104 as the retinal return echo as distinguished from the multiple return echoes 120 will be provided. The third identification method uses a property of the multiple return echoes that they have a higher attenuation rate than the retinal return echo when the gains of the high-intensity signals of both the return echoes are decreased (i.e., the crest values of the multiple return echoes are more susceptible to the gain adjustment than those of the retinal return echo). The control unit 10 receives a predetermined number of the signals of the return echoes from the ultrasonic probe 2, and then decreases the gains automatically. The return echoes that have a higher attenuation rate than the retinal return echo 104 are identified as the multiple return echoes 120. On the other hand, the return echo that has an attenuation rate almost equal to that of the retinal return echo is identified as a part of the retinal return echo 104.

The third identification method includes a case where the examiner adjusts the gains. The examiner decreases the gains using the gain adjustment switch 4a, adjusting the gains so that the return echoes 102 and 110 that are the first and second ones respectively from the anterior-segment side exceed the detection level 106a, and the return echo that shows the highest peak among the return echoes that appear subsequent to the return echo 110 reaches the detection level 106b. During the adjustment, the height of the waveforms of the multiple return echoes (the peak of the high-intensity signals) lowers at a rate higher than the height of the waveform of the retinal return echo, so that the signals of the return echoes in front of the return echo that reaches the detection level 106b are identified as the multiple return echoes. The detection levels 106a and 106b may be adjusted also by the use of the detection level-changing switch 35.

Mixed use of the first, second and third identification methods more improves accuracy in distinguishing the multiple return echoes from the retinal return echo.

While described above is a case where the switching between the phakic eye measurement mode and the IOL implanted eye measurement mode is performed with the use of the switch 34, accurate measurement is achieved with more efficiency if the switching is arranged to be performed automatically. A description of the automatic switching to the IOL implanted eye measurement mode will be provided hereinafter.

The control unit 10 determines whether the examinee's eye is a phakic eye or an IOL implanted eye based on whether or not the property to be shown by the signals of the multiple return echoes is shown in the return echoes. To be specific, the control unit 10 makes a search of the return echoes stored in the memory 14 from the retinal side. During the search, the control unit 10 makes identification of the retinal return echo in the same manner as the second identification method based on the predetermined distance Δd that is the criterion for determining the extent of the retinal return echo. Next, the control unit 10 makes a search of the return echoes from the corneal side. During this search, if the eye is a phakic eye, the rising edges of the four return echoes of the corneal return echo 102, the return echo 103a from the front surface of the crystalline lens, the return echo 103b from the rear surface of the crystalline lens, and the retinal return echo 104 (respectively the positions 107, 108a, 108b, and 109 shown in FIG. 4) are detected. Meanwhile, if the eye is an IOL implanted eye, the rising edges of a plurality of the return echoes of the multiple return echoes 120 (the positions 121a, 121b and 121c shown in FIG. 5) are detected in addition to the rising edges of the corneal return echo 102, the IOL return echo 110 and the retinal return echo 104. Then, the control unit 10 determines the eye as a phakic eye when there are four rising edges of the return echoes, and determines the eye as an IOL implanted eye when there are five or more rising edges of the return echoes according to the determination, either the phakic eye measurement mode or the IOL implanted eye measurement mode is automatically set, and its result is displayed on the screen of the display panel 3. It is to be noted that a criterion for determining whether the eye is a phakic eye or an IOL implanted eye according to the number of the rising edges of the return echoes, which is made by the control unit 10, is prestored in the memory 16.

It is also preferable that the determination of the examinee's eye as a phakic eye or an IOL implanted eye is made by using the periodicity that is a property shown uniquely by the signals of the multiple return echoes. The example of such determination is explained referring to FIGS. 4 and 5. The control unit 10 calculates the distance D between the corneal return echo 102 and the return echo that appears secondarily from the corneal side, calculates a distance (D2) between the return echoes that appear in the vicinity of the position P1 or appear interposing the position P1, the position P1 being located a predetermined distance W apart from the corneal position, and compares the distance D and the distance D2. If the distance D2 is almost equal to the distance D, the control unit 10 identifies the return echoes in the vicinity of the position P1 as the multiple return echoes produced by the IOL, and performs analysis in the IOL implanted eye measurement mode. If the distance D2 is longer than the distance D, the eye is determined as a phakic eye.

Since the types of the examinee's eye is automatically determined in the above-described cases, it is unnecessary for the examiner to determine whether the examinee's eye is a phakic eye or an IOL implanted eye. Accordingly, an examiner unaccustomed to the examination can perform the measurement with ease.

Next, a description of the operation of the apparatus at the time of the actual measurement will be provided. When the examinee has an IOL implanted eye, the examiner chooses the IOL implanted eye measurement mode using the switch 34 (or, when the return echoes are sampled, whether or not the examinee's eye is an IOL implanted eye is automatically determined). After establishing conditions for the measurement, the examiner depresses the foot switch 9 (or the measurement switch 39) to initiate retrieving the measurement data. The probe 2 is brought into contact with the cornea of the examinee's eye in this state, the ultrasonic wave transmitted from the transducer 12 is returned from the constituent parts inside the examinee's eye, and the return echoes therefrom are received by the transducer 12.

The return echoes received by the transducer 12 are sampled at predetermined extremely-short time intervals, and are stored in the sampling memory 14. The control unit 10 controls the display panel 3 to successively draw plots based on the return echoes stored in the sampling memory 14, the plots being images of the return echoes where the horizontal axis indicates a distance. Then, based on the waveform data stored in the sampling memory 14, the control unit 10 identifies the rising positions of the return echoes as the corneal position, the IOL position and the retinal position by using the first identification method, the second identification method or the third identification method (alternatively, by using an identification method of a combination of these methods). Accordingly, the ocular axial length is calculated based on the corneal position and the retinal position, and the measurement result is displayed on the display panel 3.

The foregoing description of the preferred embodiment of the invention has been presented for purposes of illustration and description. It is not intended to be exhaustive or to limit the invention to the precise form disclosed, and modifications and variations are possible in the light of the above teachings or may be acquired from practice of the invention. The embodiment chosen and described in order to explain the principles of the invention and its practical application to enable one skilled in the art to utilize the invention in various embodiments and with various modifications as is suited to the particular use contemplated. It is intended that the scope of the invention be defined by the claims appended hereto, and their equivalents.

What is claimed is:

1. A method for measuring an ocular axial length of an examinee's eye with an ophthalmic ultrasonic diagnosing apparatus, the apparatus comprising: an ultrasonic probe for A-mode measurement comprising a transducer that is arranged to emit an ultrasonic wave toward the inside of the eye, and receive return echoes from constituent parts inside the eye; and an analysis unit that is arranged to identify, by analyzing signals of the received return echoes, the respective return echo signals as a return echo signal from a cornea of the eye, a return echo signal from an intraocular lens that is implanted in the eye, multiple return echo signals that are produced from the return echo signals that repeatedly return between the intraocular lens and the transducer, and a return echo signal from a retina of the eye, while distinguishing the retinal return echo signal from the multiple return echo signals based on at least one of a property shown by the multiple return echo signals and a property shown by the retinal return echo signal, and calculate the ocular axial length based on the corneal return echo signal and the retinal return echo signal, the method comprising:
   identifying, via the analysis unit, the retinal return echo signal by at least one of:
      a first method for distinguishing, based on periodicity of the return echo signals that appear subsequent to the intraocular lens return echo signal and at a retinal side, the retinal return echo signal from the multiple return echo signals;
      a second method for distinguishing, based on a property shown by the retinal return echo signal that is obtained by making a search of the return echo signals sequentially from the retinal side to an intraocular-lens side, the retinal return echo signal from the multiple return echo signals; and
      a third method for distinguishing, based on a difference in attenuation between the retinal return echo signal and the multiple return echo signals, the difference being made when gains of the signals are adjusted, the retinal return echo signal from the multiple return echo signals,
   wherein the multiple return echo signals appear subsequent to the return echo signal from the intraocular lens and prior to a boundary position between the retina and a vitreous body, and
   wherein the retinal return echo signal appears subsequent to the boundary position.

2. The method according to claim 1, wherein the first method comprises a method for distinguishing the retinal return echo signal from the multiple return echo signals based on a condition whether distances among the return echo signals that appear subsequent to the intraocular lens return echo signal and at the retinal side appear periodically at regular intervals compared to a distance between the corneal return echo signal and the intraocular lens return echo signal.

3. The method according to claim 2, wherein in the first method, the retinal return echo signal is distinguished from the multiple return echo signals further based on a condition whether waveforms of the return echo signals that appear subsequent to the intraocular lens return echo signal and at the retinal side have widths that are equal to each other.

4. The method according to claim 1, wherein the second method comprises a method for distinguishing the retinal return echo signal from the multiple return echo signals based on one of:
   a result of comparison of each distance among the return echo signals at a predetermined intensity level that are obtained by making the search of the return echo signals from the retinal side, with a preestablished distance; and
   a result of comparison of each width of waveforms of the return echo signals that are obtained by making the search of the return echo signals from the retinal side, with a width of a waveform of the intraocular lens return echo signal.

5. A method for measuring an ocular axial length of an examinee's eye with an ophthalmic ultrasonic diagnosing apparatus, the apparatus comprising: an ultrasonic probe for A-mode measurement comprising a transducer that is arranged to emit an ultrasonic wave toward the inside of the eye, and receive return echoes from constituent parts inside the eye; and an analysis unit that is arranged to identify, by analyzing signals of the received return echoes, the respective return echo signals as a return echo signal from a cornea of the eye, a return echo signal from an intraocular lens that is implanted in the eye, multiple return echo signals that are produced from the return echo signals that repeatedly return between the intraocular lens and the transducer, and a return echo signal from a retina of the eye, while distinguishing the retinal return echo signal from the multiple return echo signals based on at least one of a property shown by the multiple return echo signals and a property shown by the retinal return echo signal, and calculate the ocular axial length based on the corneal return echo signal and the retinal return echo signal, the method comprising:
   identifying, via the analysis unit, the retinal return echo signal by a first method for distinguishing, based on periodicity of the return echo signals that appear subsequent to the intraocular lens return echo signal and at a retinal side, the retinal return echo signal from the multiple return echo signals,
   wherein the multiple return echo signals appear subsequent to the return echo signal from the intraocular lens and prior to a boundary position between the retina and a vitreous body, and
   wherein the retinal return echo signal appears subsequent to the boundary position.

* * * * *